US00PP16549P2

(12) United States Plant Patent
van Noort

(10) Patent No.: US PP16,549 P2
(45) Date of Patent: May 16, 2006

(54) ***ASTRANTIA* PLANT NAMED 'MOULIN ROUGE'**

(50) Latin Name: ***Astrantia* spp. hybrid**
Varietal Denomination: Moulin Rouge

(76) Inventor: Marco van Noort, Wasbeeklaan 13, Warmond (NL), 2361 HG ( * ) Notice: Subject to any disclaimer, the term of this patent is extended or adjusted under 35 U.S.C. 154(b) by 102 days.

(21) Appl. No.: 11/057,624

(22) Filed: Feb. 14, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—Penny J. Aguirre

(57) ABSTRACT

A new cultivar or *Astrantia* 'Moulin Rouge' characterized by its large dark red-purple inflorescences, peduncles, and pedicels and its long bloom season. 'Moulin Rouge' is a repeat bloomer with three heavy flushes of bloom from early June to mid September.

2 Drawing Sheets

Botanical classification: *Astrantia* spp. hybrid.
Variety denomination: 'Moulin Rouge'.

BACKGROUND OF THE INVENTION

The present invention relates to a new and distinct cultivar of *Astrantia* or Masterwort, botanically of hybrid origin and known as *Astrantia* 'Moulin Rouge' and will be referred to hereinafter by its cultivar name, 'Moulin Rouge'.

The inventor discovered the new cultivar, 'Moulin Rouge', in a cultivated area of his nursery in the summer of 2000. The new cultivar was derived as a naturally occurring chance seedling. The parentage is unknown, however the cultivars *Astrantia major* 'Claret' (not patented), *Astrantia major* 'Hadspen Blood' (not patented), and unnamed selections of hybrid *Astrantia* were growing in the vicinity and are possible parents.

'Moulin Rouge' was selected as unique for its dark red-purple inflorescences, its dark red-purple peduncles and pedicels and in particular for its long bloom season. It differs from its closest comparison cultivar, 'Hadspen Blood' in that 'Moulin Rouge' has larger, darker colored inflorescences and peduncles and blooms for an additional two months.

Asexual reproduction of the new cultivar was first accomplished by in vitro propagation under the direction of the inventor in Rijswijk, The Netherlands in 2002. The characteristics of this cultivar have been determined to be stable and are reproduced true to type in successive generations.

SUMMARY OF THE INVENTION

The following traits have been repeatedly observed and are determined to be the characteristics of 'Moulin Rouge'. These characteristics in combination distinguish 'Moulin Rouge' as a new and distinct cultivar of *Astrantia*. 'Moulin Rouge' has not been observed under all possible environmental conditions and the phenotype may vary under different growing conditions without variance in genotype.

1. Large, dark purple red flowers with contrasting white stamens and deep purple bracts with very dark tips.

2. Dark purple red peduncles and pedicels held on sturdy stems.
3. Long blooming with three repeat flushes of bloom from early June to mid September in The Netherlands.
4. Upright plant habit and tolerant to wind and rain.

BRIEF DESCRIPTION OF THE DRAWING

The accompanying colored photographs illustrate the overall appearance and distinct characteristics of one-year old plant of the new *Astrantia*.

The photograph on the first sheet provides a view of a typical flowering plant.

The photograph on the top of the second sheet is a close-up of the foliage and

The photograph on the bottom of the second sheet is a close-up of a flower.

The colors in the photographs are as close as possible with the photographic and printing technology utilized. The color values cited in the detailed botanical description accurately describe the colors of the new *Astrantia*.

DETAILED BOTANICAL DESCRIPTION

The following is a detailed description of the new cultivar as grown under outdoors field conditions for one year in The Netherlands. They were grown under natural lighting with day temperatures ranging from 14° to 26° C. and night temperatures of 6° to 12° C. The color determination is in accordance with the 2001 R.H.S. Colour Chart of The Royal Horticultural Society, London, England, except where general color terms of ordinary dictionary significance are used. The descriptions were taken in September of 2004.

Botanical classification: 'Moulin Rouge' is a cultivar of *Astrantia* of hybrid origin.
Parentage: Naturally occurring chance seedling of *Astrantia*, parentage unknown.

General description:

*Blooming period.*—Long blooming, Remontant with three heavy flushes of bloom from early June to mid September.

*Plant habit.*—Herbaceous perennial, upward, vase-shaped habit in flower, erect peduncles emerge well above the basal rosette of foliage.

*Height and spread.*—Reaches about 50 to 60 cm in height and 30 cm in width.

*Hardiness.*—Cold hardy at least to U.S.D.A. Zone 6 and Heat tolerant at least to 30° C.

*Culture.*—Tolerant to a wide range of growing conditions, growing best in full sun to light shade in moist, humus-rich soils, tolerant to wind and rain.

*Disease and pest resistance.*—No susceptibility or resistance to diseases or pests common to *Astrantia* has been observed for 'Moulin Rouge'.

*Root description.*—Fibrous.

Growth and propagation:

*Propagation.*—Tissue culture or division.

*Cropping time.*—19 weeks from a rooted propagule to finished field grown division.

*Growth rate.*—Moderate.

Stem description:

*Stem shape.*—Round.

*Stem color.*—143A towards base, a color between 146A and 147A towards apex.

*Stem size.*—Average of 30 cm in length (excluding inflorescence) and 5 mm in diameter.

*Stem surface.*—Glabrous with slight sheen, slight longitudinal ribbing.

*Stem strength.*—Strong, held upright.

*Branching habit.*—Freely branched, mostly basal branching, about 5 flowering stems one a one year old plant (suitable for a one-gallon container).

Foliage description:

*Leaf division.*—Simple.

*Leaf shape.*—Palamtely lobed, reniform in outline.

*Leaf base.*—Hastate.

*Leaf apex.*—Acute.

*Leaf margin.*—Biserrate, average of 1 large tooth and 6 smaller teeth per cm, aristate.

*Leaf venation.*—Laciniate in pattern, upper veins range in color from 143A to 143B, lower veins range in color from 143B to 143C.

*Leaf attachment.*—Petiolate.

*Leaf arrangement.*—Alternate.

*Leaf surface.*—Glabrous, upper and lower surfaces.

*Leaf color.*—Young; upper surface color intermediate between 137A and 147A, lower surface 137C. Mature: upper surface 137A, lower surface 137C.

*Leaf size.*—Basal leaves average 7.7 cm in length and 9.7 cm in width, stem leaves average 4.6 cm in length and 5.1 cm in width.

*Leaf number.*—Average of 20 leaves per plant, average of 10 are basal leaves.

*Petiole.*—Basal leaves: average of 8.7 cm in length, 3.5 mm in diameter, ovate in shape, glabrous texture, color 143A to 143B. Stem leaves: winged (folded), average of 1.5 cm in length, average of 3.5 mm in diameter spreading to 1.2 cm in width when spread open, color 144B striped with 143B.

Flower description:

*Inflorescence type.*—Compound umbel of numerous campanulate flowers subtended by showy involucral bracts.

*Lastingness of inflorescence.*—Average of 12 days, self cleaning.

*Inflorescence size.*—Terminal: average of 8.7 cm in height and 3.7 cm in diameter. Secondary: average of 4.5 cm in height and 2.5 cm in diameter.

*Inflorescence fragrance.*—Moderate, unpleasant.

*Flower number.*—Average of 75 per umbel, average of 11 umbels per inflorescence, average of 825 flowers per flowering stem.

*Flower form.*—Campanulate.

*Flower aspect.*—Upright.

*Flower bud size.*—Average of 4 mm in length, average of 1.5 mm in diameter.

*Flower bud color.*—145C to 145D, apex 187A.

*Flower bud shape.*—Obovate with flattened apex.

*Flower form.*—Campanulate.

*Flower size.*—Average of 7 mm in depth and 2 mm in diameter.

*Corolla features.*—Petals are un-fused and upright.

*Petal number.*—5.

*Petal shape.*—Ovate.

*Petal color.*—Opening and fully open, upper and lower surfaces: 155A on basal half, 187C on the distal half.

*Petal surface.*—Dull, glabrous.

*Petal margins.*—Entire.

*Petal apex.*—Narrowly apiculate.

*Petal size.*—Average of 2 mm in length and 0.8 mm in width.

*Calyx form.*—Campanulate, sepals un-fused, overlapping at base, held upright.

*Calyx size.*—Average of 1.5 mm in length and 2 mm in diameter.

*Sepal number.*—5.

*Sepal shape.*—Ovate.

*Sepal margin.*—Entire.

*Sepal size.*—Average of 1.5 cm length, 0.8 mm in width (at base).

*Sepal surface.*—Dull, glabrous.

*Sepal apex.*—Acute.

*Sepal base.*—Cuneate.

*Sepal color.*—Opening and fully open, upper and lower surfaces:: 187B, becoming apex 187A towards apex.

*Peduncle size.*—Terminal: average of 7.2 cm in length and 2.5 mm in diameter, Secondary: average of 3.2 cm in length and 2.5 mm in diameter.

*Peduncle strength/aspect.*—Strong, terminals held upright, secondary held at an average of 40° from stem.

*Peduncle color.*—146A to 147A, striped with N186C.

*Pedicel size.*—Average of 6 mm in length and 0.3 mm in width.

*Pedicel strength/aspect.*—Strong, terminal held upright, secondary held about 60° from stem.

*Pedicel color.*—186D.

*Inflorescent leaves.*—About 3 to 5 per inflorescent, sessile, about 2.5 cm in length and 3.5 cm in width, palmately lobed with acute apex, entire margin and cuneate base, color 137A on upper surface and 137C on lower surface.

Involucral bracts:

*Bract number.*—About 20.

*Bract shape.*—Narrowly elliptic.

*Bract size.*—About 1.8 cm in depth and 4 mm in width.

*Bract color.*—Upper surface: color is intermediate between 59A and N186D with a base 156C to 156D and tip N186C; Lower surface: N186D with a base of 145D and tip N186C to N186A.

*Bract texture.*—Glabrous, dull.

*Bract apex.*—Acute.

*Bract margins.*—Cuneate.

Reproductive organs:

*Gynoecium.*—2 pistils, about 3 mm in length, stigma is club-shaped and N186A in color, style is about 2.8 mm in length, N186A in color, becoming lighter towards base, ovary is 143B in color.

*Androcoecium.*—5 stamens, anthers are dorsifixed, elliptic in shape, about 1 mm in length and 164C in color, filament is about 3.5 mm in length and 155A in color and 187C near apex, pollen is low in abundant and 157C to 157D in color.

*Fruit/seeds.*—Sterile under the conditions tested; no fruit set (or seeds) have been observed to date.

I claim:

1. A new and distinct cultivar of *Astrantia* plant named 'Moulin Rouge' as herein illustrated and described.

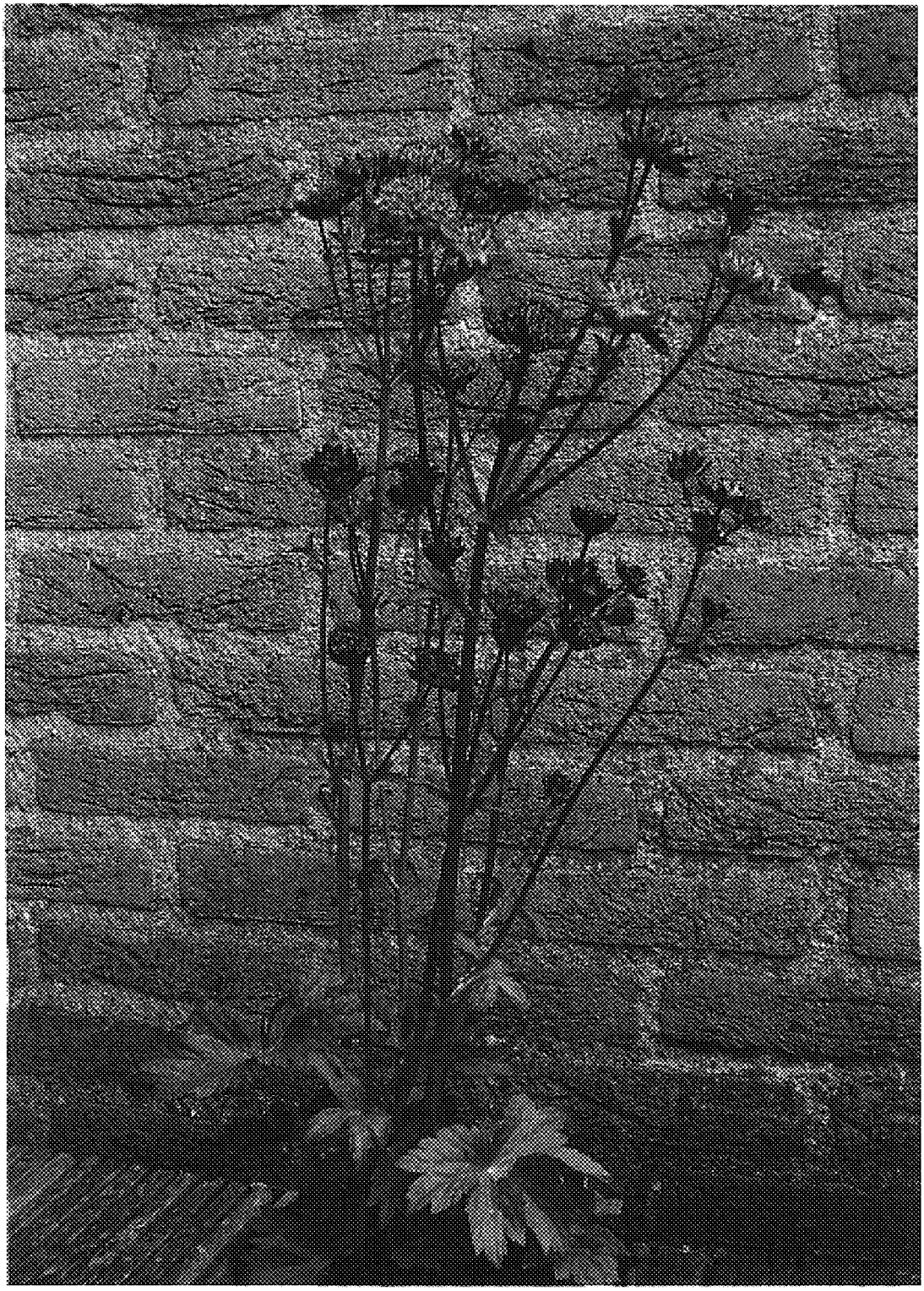

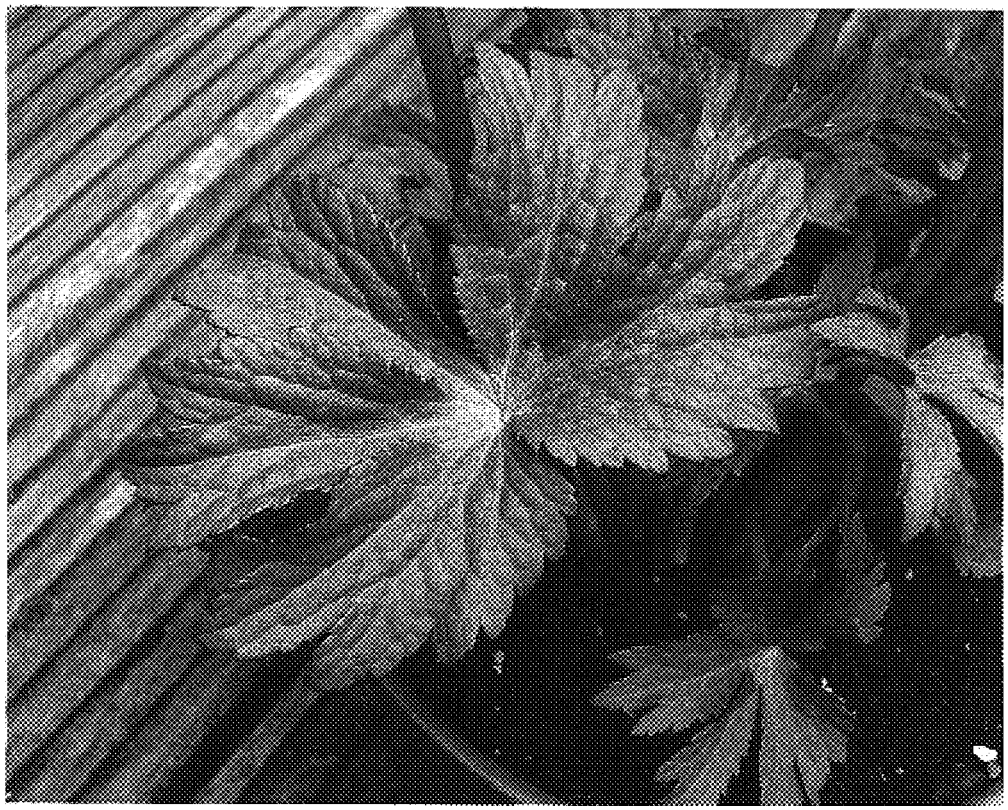
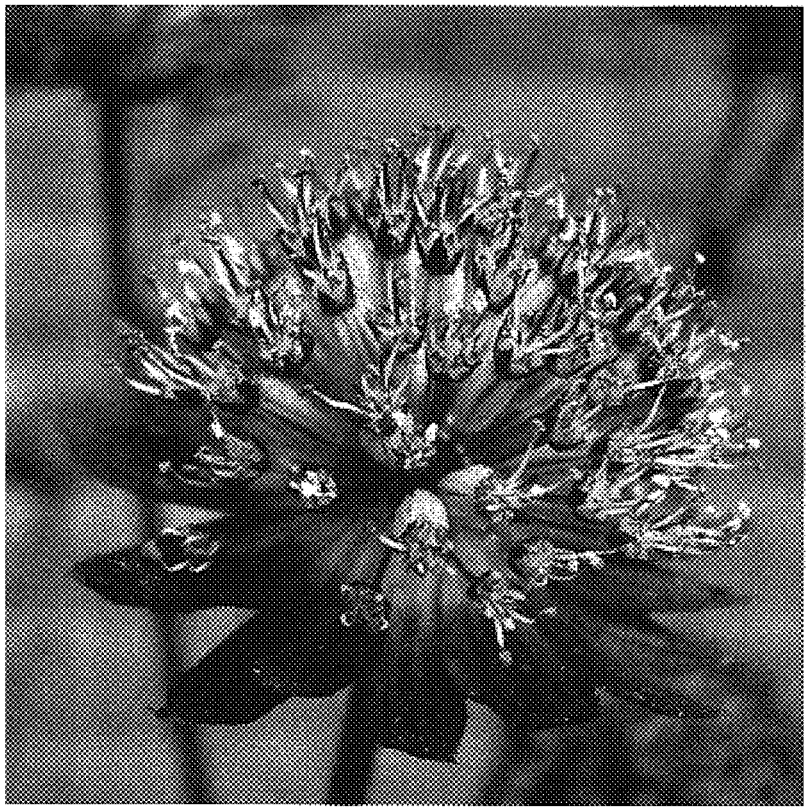

* * * * *